United States Patent
Chieffo et al.

(10) Patent No.: US 9,513,213 B2
(45) Date of Patent: Dec. 6, 2016

(54) SYSTEM AND METHOD OF DETERMINING ROCK PROPERTIES USING TERAHERTZ-BAND DIELECTRIC MEASUREMENTS

(71) Applicants: Logan Chieffo, Cambridge, MA (US); Richard Averitt, Newton, MA (US); Andrew Speck, Milton, MA (US); Michael M. Herron, Cambridge, MA (US); A. Ballard Andrews, Wilton, CT (US); Ronald E. G. Van Hal, Belmont, MA (US)

(72) Inventors: Logan Chieffo, Cambridge, MA (US); Richard Averitt, Newton, MA (US); Andrew Speck, Milton, MA (US); Michael M. Herron, Cambridge, MA (US); A. Ballard Andrews, Wilton, CT (US); Ronald E. G. Van Hal, Belmont, MA (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 498 days.

(21) Appl. No.: 13/962,816

(22) Filed: Aug. 8, 2013

(65) Prior Publication Data

US 2015/0046090 A1     Feb. 12, 2015

(51) Int. Cl.
*G01N 21/3586* (2014.01)
*G01N 33/24* (2006.01)

(52) U.S. Cl.
CPC ........ *G01N 21/3586* (2013.01); *G01N 33/241* (2013.01)

(58) Field of Classification Search
CPC ............. G01N 21/35; G01N 21/3581; G01N 21/3586; G01N 33/24; G01N 33/241
See application file for complete search history.

(56) References Cited

U.S. PATENT DOCUMENTS 7,675,036 B2 * 3/2010 Taday .................. G01S 13/887
250/341.1

OTHER PUBLICATIONS

Scales et al., Millimeter Wave Spectroscopy of Rocks and Fluids, 2006, Applied Physics Letters 88, 3 pp.*
Ervasti, et al., "A Study on the Resolution of a Terahertz Spectrometer for the Assessment of the Porosity of Pharmaceutical Tablets", Applied Spectroscopy, vol. 66 (3), 2012, pp. 319-323.
Li, et al., "Precisely optical material parameter determination by time domain waveform rebuilding with THz time-domain spectroscopy", Optics Communications, vol. 283, 2010, pp. 4701-4706.
O'Hara, et al., "Enhanced terahertz detection via ErAs:GaAs nanoisland superlattices", Applied Physics Letters, vol. 88, 2006, 3 pgs.
Pupeza, et al., "Highly accurate optical material parameter determination with THz time-domain spectroscopy", Optics Express, vol. 15 (7), Apr. 2, 2007, pp. 4335-4350.
Wang, et al., "A simplified model for the dielectric function of three-component composite materials", Physica A: Statistical Mechanics and Its Applications, vol. 275 (1), 2000, pp. 256-261.
Young Kim, KI, "Recent Optical and Photonic Technologies", Electrical and Electronic Engineering, 2010, pp. 231-250.

* cited by examiner

*Primary Examiner* — Toan Le
(74) *Attorney, Agent, or Firm* — Daniel S. Matthews (57) ABSTRACT

A method of analyzing physical properties of a sample includes obtaining the sample and obtaining an electromagnetic spectrum of the sample using terahertz spectroscopy. A sample complex permittivity is computed from the electromagnetic spectrum of the sample. The method further includes estimating the constituents and the constituent fractions and computing an estimated effective complex permittivity based upon a model and the constituent fractions. The method further includes comparing the computed sample complex permittivity with the estimated effective complex permittivity in order to determine the physical properties the sample.

30 Claims, 10 Drawing Sheets

SYSTEM AND METHOD OF DETERMINING ROCK PROPERTIES USING TERAHERTZ-BAND DIELECTRIC MEASUREMENTS

BACKGROUND

Measurements of the dielectric constants of materials at different frequencies are used in many different measurement schemes. For example, capacitance measurements at low frequencies are used to distinguish between oil and water. In the oil and gas sectors, for example, dielectric scanners may measure these constants at frequencies up to 1-2 GHz to determine water volume and rock properties. In addition, Fourier transform infrared ("FTIR") measurements in the infrared region may be used to determine mineralogy of core samples.

Other measurements demanding sample preparation, such as those utilizing helium pycnometry are unable to provide accurate results in the case of unconventional oil and gas reservoirs that possess low permeability. Nuclear magnetic resonance (NMR) based measurements of pore volume may be used, but are often limited by the small pores in unconventional samples that cause fast relaxation times in the NMR signal that are difficult to accurately measure. Commercial measurements today are generally based on utilizing crushed samples but these techniques both add uncertainty due to the crushing process and also are destructive measurements may demand extensive sample preparation.

Other techniques for identifying the mineralogy of core samples include diffuse reflective infrared Fourier transform spectroscopy (DRIFTS). However, due to similarity of FTIR spectrum of smectite and illite samples, DRIFTS is unable to accurately distinguish between these notable constituents of shale beds. Similar issues in accurately determining the concentrations of illite and smectite have been observed in measurements taken with X-ray diffraction (XRD).

SUMMARY

Illustrative embodiments of the present disclosure are directed to a method for determining rock properties using terahertz band dielectric measurements. The method includes obtaining an unknown sample and obtaining an electromagnetic spectrum of the unknown sample using terahertz spectroscopy. An unknown sample complex permittivity is computed from the electromagnetic spectrum of the unknown sample. The method further includes estimating the constituents and constituent fractions and computing an estimated effective complex permittivity based upon a model and the constituent fractions. The method further includes comparing the computed unknown sample complex permittivity with the estimated effective complex permittivity in order to determine the physical properties the unknown sample.

Also, various embodiments of the present disclosure are directed to a system for determining rock properties using terahertz band dielectric measurements. The system includes a THz spectrometer that may obtain a THz spectrum of an unknown sample. The system also includes an analysis module that receives an electromagnetic spectrum of the unknown sample. In accordance with one or more embodiments, the electromagnetic spectrum includes a terahertz spectrum and the analysis module may compute an unknown sample complex permittivity from the electromagnetic spectrum of the unknown sample. The analysis module may further estimate constituents and constituent fractions of the unknown sample. The analysis module may further compute an estimated effective complex permittivity based upon a model and the constituent fractions and compare the computed unknown sample complex permittivity with the estimated effective complex permittivity in order to determine the physical properties the unknown sample.

Illustrative embodiments are directed to a system of determining rock properties using terahertz band dielectric measurements that includes a non-transitory computer readable medium. The computer readable medium includes computer readable program code embodied therein, that, when executed on a processor, causes the processor to receive an electromagnetic spectrum of an unknown sample and compute an unknown sample complex permittivity from the electromagnetic spectrum of the unknown sample, estimate constituents and constituent fractions of the unknown sample, compute an estimated effective complex permittivity based upon a model and the constituent fractions, and compare the computed unknown sample complex permittivity with the estimated effective complex permittivity in order to determine the physical properties the unknown sample.

Other aspects of the disclosure will be apparent from the following description and the appended claims.

DETAILED DESCRIPTION

Dielectric constant measurements can provide information such as specific resonances of constituent minerals and molecules, and thus such measurements are ideal for identifying detailed sample composition. Furthermore, trends in the collective behavior of the measured dielectric constant as a function of frequency may reveal information that can distinguish between distinct classes of materials such as oil versus water or sandstone versus clays.

In general, in accordance with one or more embodiments, the present disclosure is directed to systems and methods for the determination of rock properties using terahertz-band dielectric measurements. Different materials, e.g., rocks, minerals, fluids, etc., have substantially different dielectric properties in the terahertz (THz) frequency range (approximately 0.08 THz-10 THz). These differing responses depend, in part, on the composition and structure of the material. Thus, by measuring the dielectric constant of an unknown rock sample as a function of THz frequency, and then inverting an effective medium theory, or dielectric mixing law, the volume fractions of the constituents of an unknown sample may be determined. For example, in the case of an unknown sample, e.g., a core sample, obtained from a location that includes an unconventional oil and gas reservoir, the relative fraction of various clays may be of great importance. In accordance with one or more embodiments, the present disclosure is directed to a system and method that can determine the fraction of illite and smectite in an unconventional sample using terahertz-band dielectric measurements. In addition, in accordance with one or more embodiments, the present disclosure is directed to a system and method for determining the volume fraction of crude oil, natural gas, water, and/or rock matrix in an unknown sample using terahertz-band dielectric measurements. In addition, the systems and methods described herein may be used to determine the porosity and water saturation in a low permeability, unconventional core sample. In various embodiments, the systems and methods disclosed herein allow for the investigation of unknown rock samples in situ, meaning that, in one or more embodiments, the measurements do not involve replacing the component fluids in the sample with different components and, thus the disclosed systems and methods may be used to determine the properties of an untreated or unmodified rock sample, i.e., as it occurs in the field, including but not limited to, the identification of unmodified low permeability rock that is often present in unconventional oil and gas reservoirs.

Figure 1:
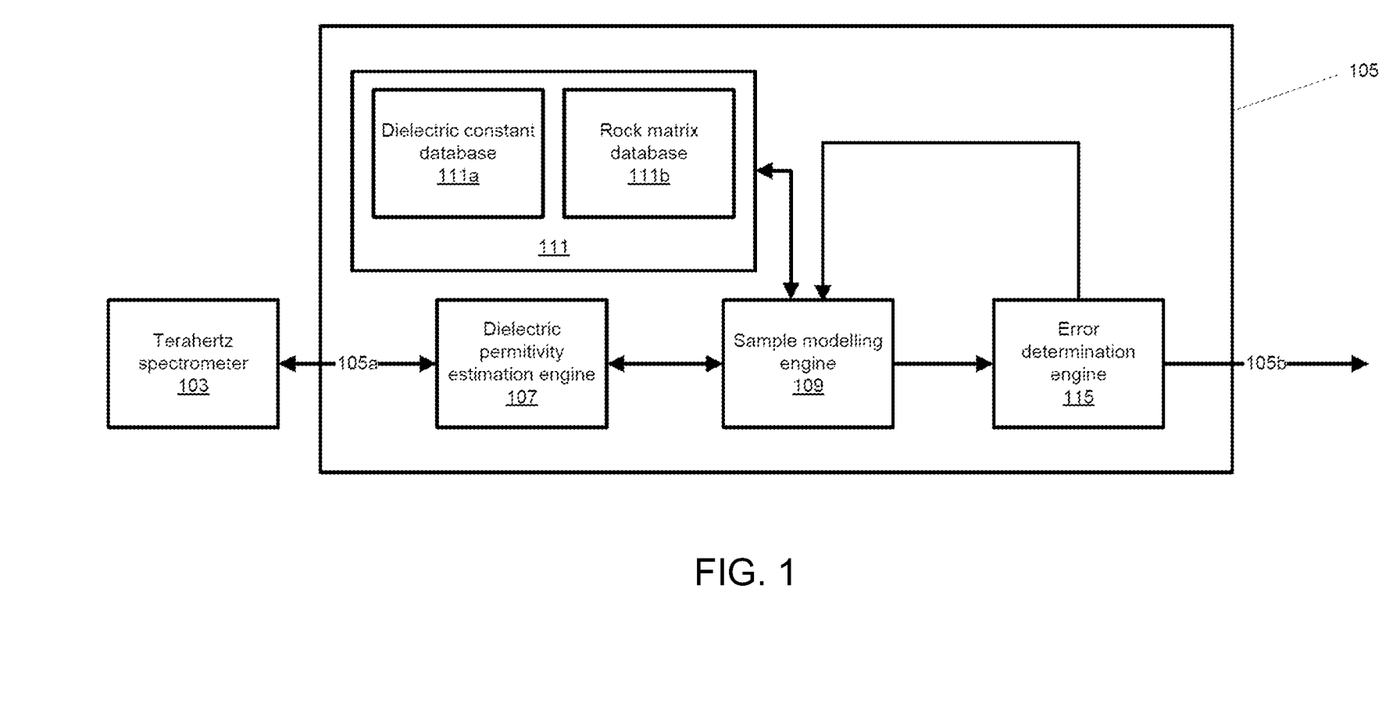
FIG. 1 shows a system in accordance with one embodiment.

FIG. 1 shows one example of a system for the determination of rock properties using terahertz-band dielectric measurements. In accordance with one or more embodiments, the system includes a terahertz spectrometer system 103 and an analysis module 105. In the examples that follow, for the sake of simplicity, a system employing a THz time domain spectrometer ("THz-TDS") system is described. However, without departing from the scope of the present disclosure, any type of THz band spectrometer may be used including, e.g., systems that employ continuous wave (CW) THz sources. In one or more embodiments, the analysis module is a module for performing numerical analysis on one or more THz-TDS spectra obtained from the THz spectrometer system 103. The analysis module may include hardware, software, or a combination of both. For example, the hardware may include a computer processor (not shown) and memory (not shown). Furthermore, in accordance with one or more embodiments, the software and/or hardware of the analysis module 105 may include a dielectric permittivity estimation engine 107, a sample modeling engine 109, an error determination engine 115, and a data repository 111. The numerical analysis and each of the engines can be implemented as software instructions (e.g., computer readable program code) that is stored in the memory and executed by the computer processor to perform various processes as described herein. Furthermore, the analysis module 105 may include one or more interfaces, e.g., interfaces 105a, 105b that may include a user interface and/or an application programming interface (API). In accordance with one or more embodiments, the interfaces include functionality to receive input and transmit output, such as to a display (not shown). For example, the input may be a THz-TDS spectrum, or more generally a THz spectrum of any kind, of one or more core samples and other information, e.g., known properties, constituents and/or known rock matrices of the core sample.

In accordance with one or more embodiments, the THz spectrometer system 103 is configured to obtain a terahertz time domain spectrum ("THz-TDS spectrum") of a rock sample obtained from the field, e.g., by way of a downhole coring tool or from cuttings retrieved during drilling. In accordance with one or more embodiments, the analysis module 105 is configured to receive a THz-TDS spectrum and to determine one or more properties of the rock sample based on the THz-TDS spectrum. More precisely, the analysis module 105 includes a dielectric permittivity estimation engine 107 that determines the complex permittivity of the sample based on the THz-TDS spectrum. Once the complex permittivity of the sample is determined by the dielectric permittivity estimation engine 107, a sample modeling engine 109 constructs a model complex permittivity based on the measured complex permittivity. In accordance with one or more embodiments, the model complex permittivity may be based on one or more external input parameters related to known physical properties of the sample that are input by a user.

The model complex permittivity may be formed from combining one or more rock constituents by way of an effective medium theory and/or a dielectric mixing law. More precisely, the model may be formed by combining two or more rock types and/or fluid types (including both oil and gas) having previously known or measured complex permitivities that are stored in the data repository 111, which itself may include a dielectric constant database 111a and a rock matrix database 111b. In one or more embodiments, the data repository 111 is any type of storage unit and/or device (e.g., a file system, database, collection of tables, or any other storage mechanism) for storing data. Further, the data repository 111 may include multiple different storage units and/or devices. The multiple different storage units and/or devices may, or may not, be of the same type or located at the same physical site. Furthermore, in accordance with one or more embodiments, the data repository 111 includes functionality to store one or more previously measured frequency dependent complex permitivities for various materials such as fluids, minerals, and rock matrix types. For example, as shown in FIG. 1, the data repository 111 may include a dielectric constant database 111a and a rock matrix database 111b that store the previously measured frequency dependent complex permitivities. In addition to being accessed from the data repository 111, the identity and/or physical properties of one or more of the constituents in the model may be input directly by a user if already known e.g., through the use of previous measurements. The use of previously known constituents may serve to increase the speed and accuracy of the computational procedure used to determine the model complex permittivity based on the measured complex permittivity.

Once an initial model is constructed using data from the data repository 111 and/or user input, an error estimation engine 115 computes the error between the model complex permittivity and the measured complex permittivity. In accordance with one or more embodiments, if the computed error is above a predetermined threshold, the volume fractions of the constituents that make up the model are adjusted and an updated model is computed by the sample modeling engine 109. The error determination engine 115 then recomputes the error between the updated model and the measured complex permittivity. This iterative process of 1) update model and 2) compute error, proceeds until the computed error drops below the predetermined threshold at which time, the error determination engine 115 outputs the model parameters, including the constituent identities and volume fractions of the model. In accordance with other embodiments, the iterative process may proceed until the model constituent values, e.g., the volume fractions, converge to stable values. Thus, the volume fractions that lead to an accurate estimate of the volume fractions and constituents that make up the sample are determined numerically by way of the analysis module 105.

While FIG. 1 shows a configuration of components, other configurations may be used without departing from the scope of the embodiments disclosed herein. For example, various components may be combined to create a single component. As another example, the functionality performed by a single component may be performed by two or more components.

Figure 2:
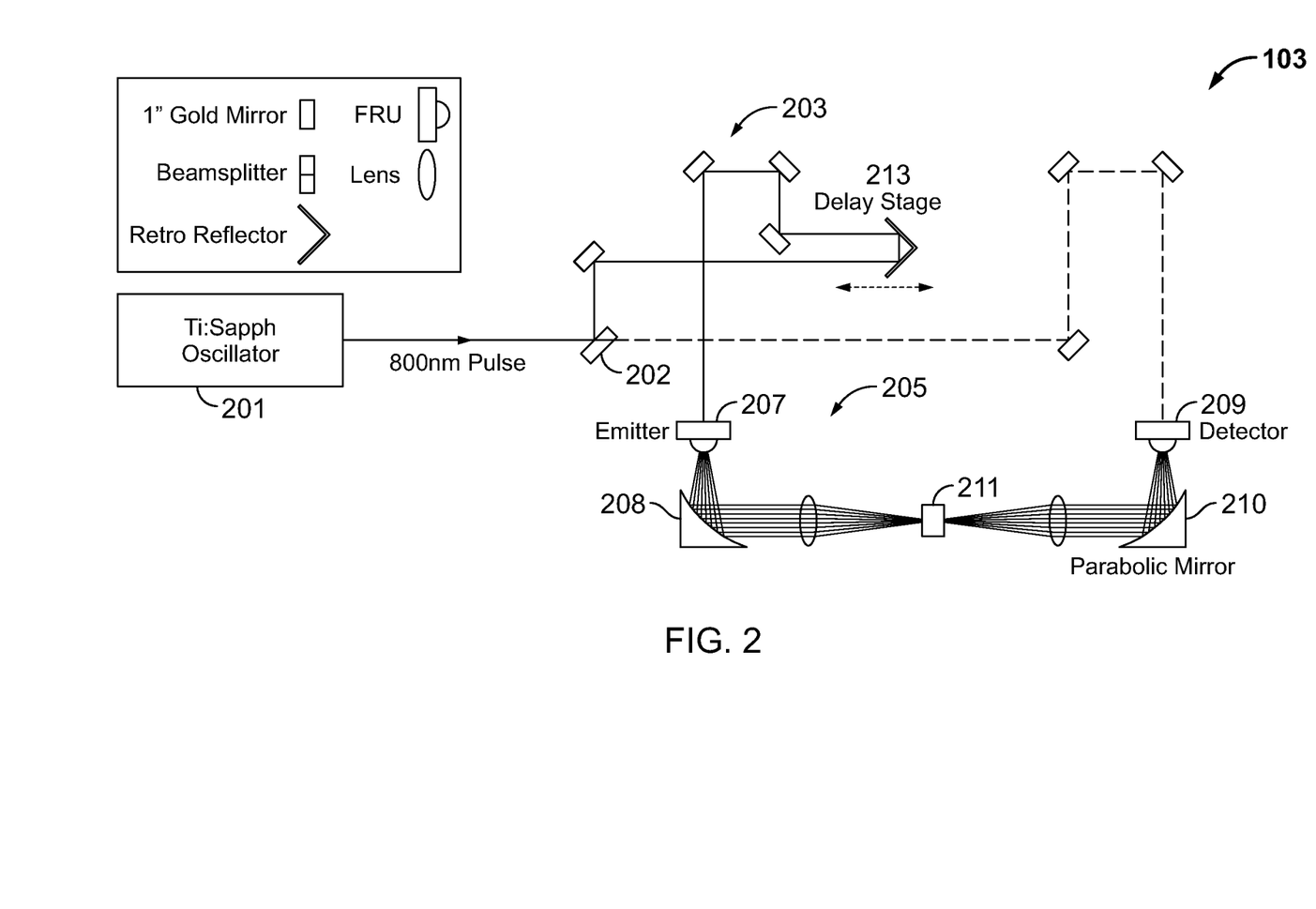
FIG. 2 shows a system in accordance with one embodiment.

FIG. 2 shows an example of a terahertz time domain spectrometer system (THz-TDS system) that, in accordance with one or more embodiments may be employed as the THz spectrometer system 103 in FIG. 1. The example shown in FIG. 2 is simply one example, and one of ordinary skill in the art having the benefit of this disclosure will recognize that any other terahertz spectrometer may be used that can measure dielectric constants of samples within the terahertz frequency band (e.g., microwave based continuous-wave sources) without departing from the scope of the present disclosure. In this example, an oscillator 201, e.g., a pulsed Ti:Sapphire laser, generates pulses on the order of 10 to 200 fs in duration with a center wavelength of 750 to 840 nm and a repetition rate of 70 to 100 MHz. The pulse train from oscillator 201 is split into two by beam splitter 202 and directed by various mirrors into arm 203 and arm 205 of the spectrometer. In accordance with one or more embodiments, the power in arms 203 and 205 may be approximately 10 mW-200 mW. The portion of the pulsed beam in arm 203 is used to pump a THz emitter 207 (e.g., a photoconductive antenna) to generate a THz pulse that is directed to, and focused onto, the sample 211 using, for example, a parabolic mirror 208. The portion of the pulsed beam in arm 205 is used to gate, or trigger, a detector 209 at a variable time that is determined by the optical path length of the arm 205, which may be set, or scanned by delay stage 213.

In accordance with one or more embodiments, the emitter 207 includes two gold strip-lines (not shown), separated by 10 μm to 1 mm, that are patterned on a gallium arsenide (GaAs) substrate. The femtosecond pulses from the oscillator 201 are tightly focused in the center of the strip-lines while a bias voltage is applied across the strip-lines. In accordance with one or more embodiments, the bias voltage is used to accelerate photo-induced free carriers to generate a resulting current that generates a THz pulse and may be approximately of 50 V-1 kV. The detector 209 is configured to receive the THz pulse after it has passed through the sample 211. In this example, another parabolic mirror 210 is used to direct the pulse onto the detector 209. The detector 209 operates on inverse principles and includes a dipole antenna of length 5 to 100 μm. In one such embodiment, instead of biasing the antenna externally, the THz pulse's electric field generates a current that is measured and is proportional to the electric field at the specific temporal delay. In accordance with one or more embodiments, the detector is patterned on a custom grown substrate of erbium arsenide (ErAs) nanoisland superlattices embedded in gallium arsenide (GaAs). Furthermore, in accordance with one or more embodiments, the design of the superlattices may be optimized to have a minimum carrier lifetime. After passing through the sample 211, the femtosecond pulses are tightly focused in the gap of the dipole antenna of detector 209. In accordance with one or more embodiments, a lock-in amplifier (not shown) measures the current generated in the dipole antenna gap of the detector 209 due to the incoming THz pulse. Furthermore, in one or more embodiments, several high resistivity silicon hyper-hemispheres (not shown) are pressed to the back of the substrates of emitter 207 and detector 209 in order to efficiently couple the THz radiation into and out from the emitter and detector antennas, respectively. The resulting THz pulses contain frequency content from 0.1-3 THz.

Figure 3A:
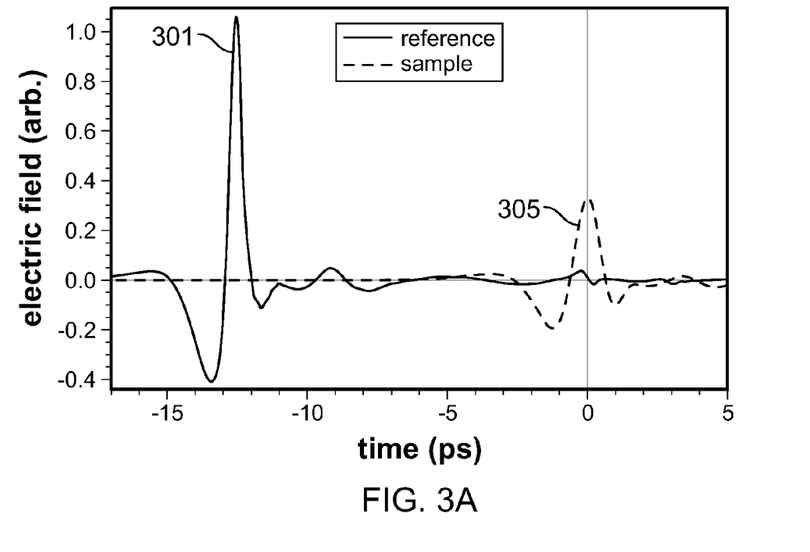
FIGS. 3A-3C show examples of THz-TDS data in accordance with one or more embodiments.

FIG. 3A shows an example of a THz-TDS spectrum acquired by a THz-TDS system in accordance with one or more embodiments of the disclosure. More specifically, the THz-TDS spectrum is the electric field amplitude as a function of time as measured by a THz detector, such as detector 209, shown in FIG. 2. As such, a THz-TDS spectrum includes both amplitude and phase information, both of which may be obtained from the Fourier transform of the THz-TDS spectrum. In FIG. 3A, spectrum 301 is a THz-TDS spectrum obtained for a reference sample, e.g., a THz-TDS spectrum obtained with a THz-TDS system having no rock sample in the path of the THz pulse. Furthermore, spectrum 305 is a THz-TDS spectrum obtained for an unknown sample, e.g., a THz-TDS spectrum obtained with a THz-TDS system having an unknown rock sample in the path of the THz pulse.

Figure 3B:
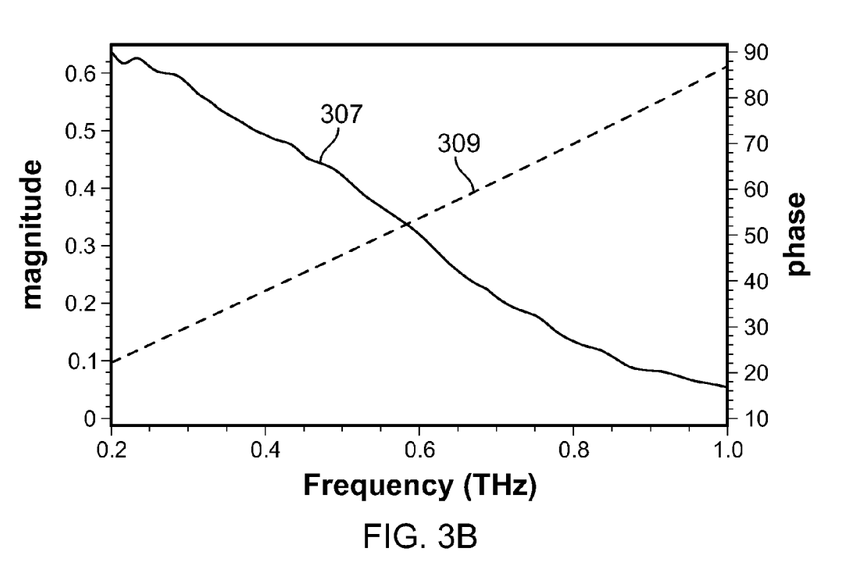
Figure 3C:
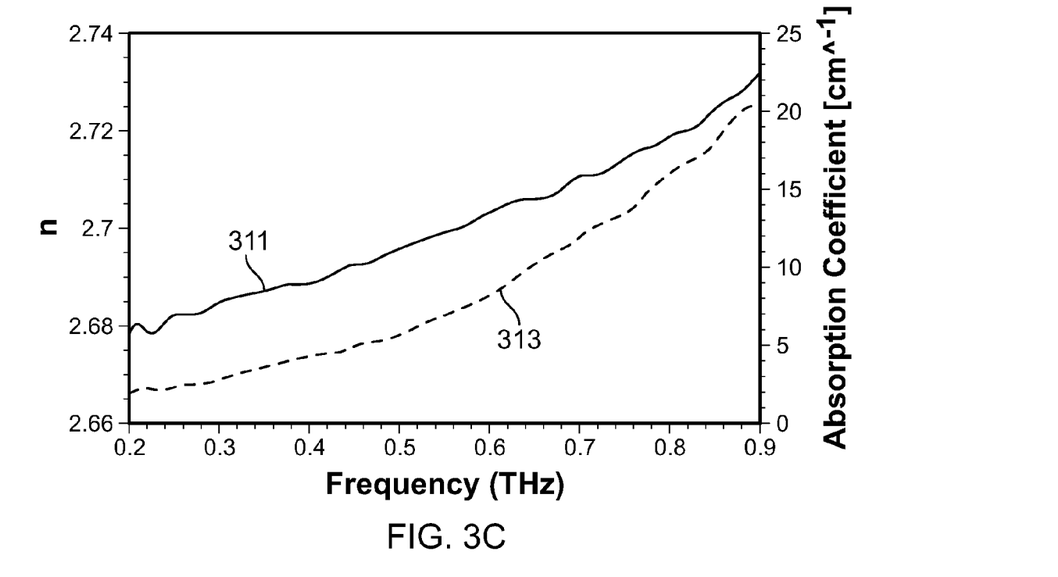
Figure 4A:
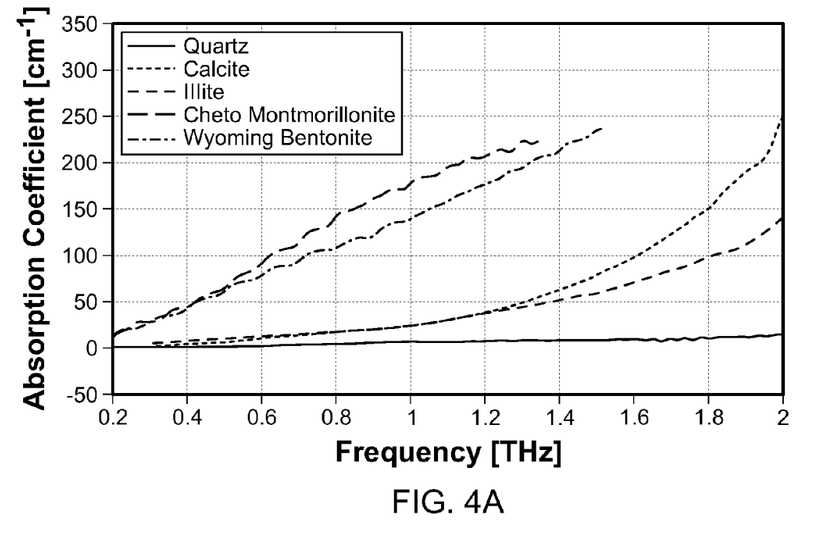
FIGS. 4A-4B show examples of frequency dependent index of refraction measurements and frequency dependent absorption coefficient measurements made using reference samples of known composition, in accordance with one embodiment.
Figure 4B:
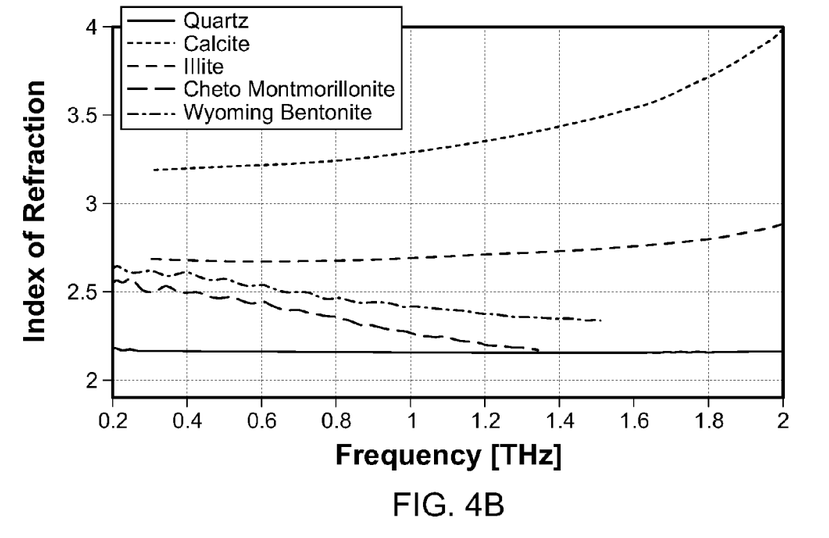
Figure 5A:
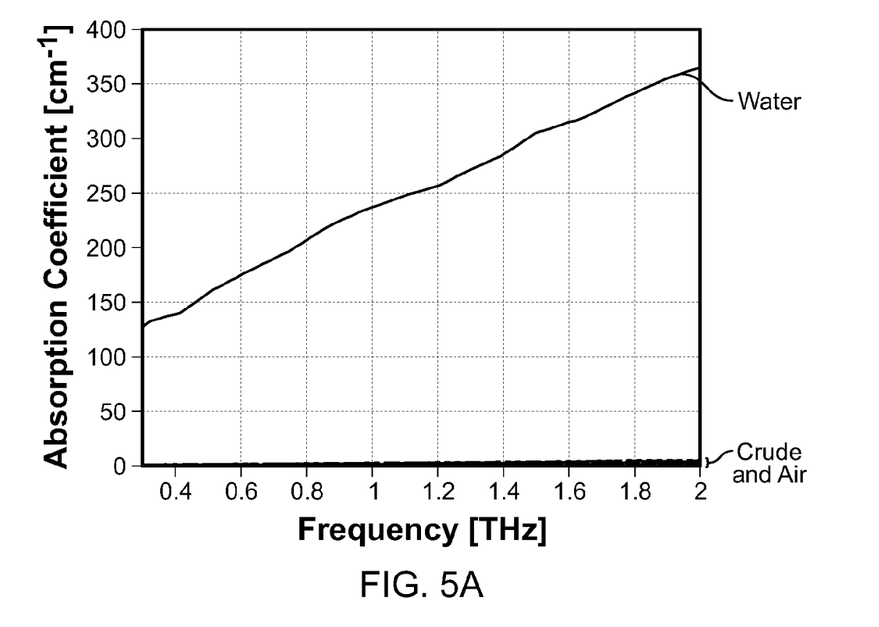
FIGS. 5A-5B show examples of frequency dependent index of refraction and frequency dependent absorption coefficient measurements made using reference samples of known composition, in accordance with one embodiment.
Figure 5B:
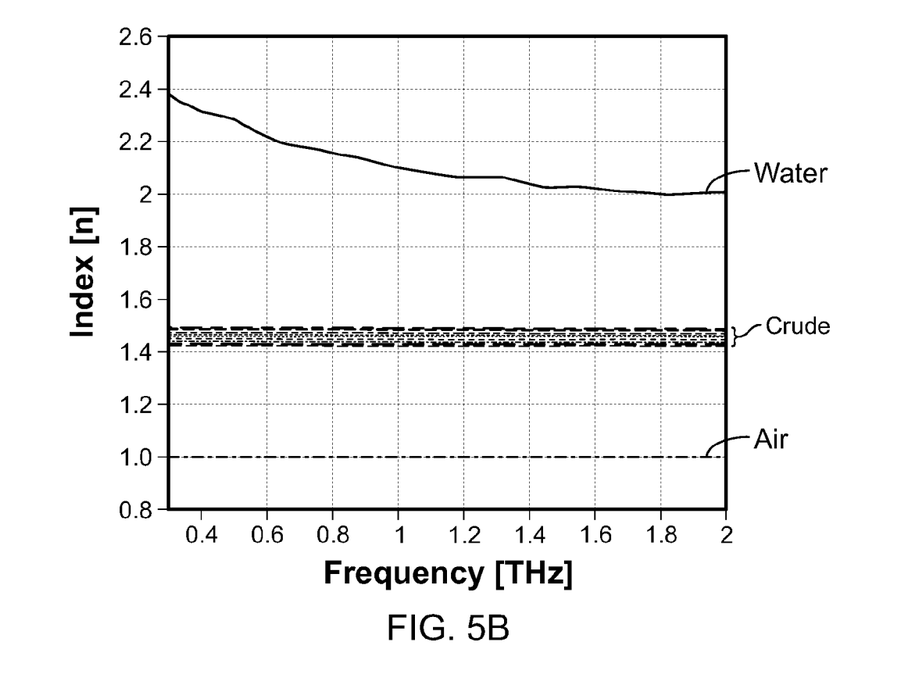

In accordance with one or more embodiments, the physical parameters of the sample may be determined from THz spectra, e.g., spectra similar to those shown in FIG. 3A. Furthermore, one or more embodiments of the present disclosure are not limited to the THz-TDS systems used as examples herein. For example, the THz spectra may be obtained using any type of THz spectrometer including, e.g., continuous wave (CW) microwave-based systems, or the like. In accordance with one or more embodiments, the THz-TDS spectra are used to estimate the complex index of refraction of the sample $\tilde{n}(\omega)=n(\omega)-i\kappa(\omega)$, where $n(\omega)$ is the frequency dependent (real) refractive index of the unknown sample, $\kappa(\omega)$ is the frequency dependent extinction coefficient of the unknown sample, and $\omega=2\pi f$, where f is the frequency of the electromagnetic radiation interacting with the material. Furthermore, the frequency dependent extinction coefficient $\kappa(\omega)$ can be written in terms of a frequency dependent absorption coefficient: $\alpha(\omega)=2\omega\kappa(\omega)/c_0$. FIG. 3B shows the magnitude 307 and phase 309 of the transfer function of the unknown sample obtained by dividing the Fourier transform of the sample scan by the Fourier transform of the reference scan. As is described in more detail below, the real part of the transfer function is related to $\kappa(\omega)$ of the sample, while the imaginary part of the transfer function is related to $n(\omega)$ of the sample. FIG. 3C shows the index of refraction 311, i.e., $n(\omega)$ and absorption coefficient 313, i.e., $\alpha(\omega)$ as computed from the transfer function as described in more detail below.

Furthermore, in accordance with one or more embodiments, $\tilde{n}(\omega)$ (as plotted in FIG. 3C) may be determined numerically from a measured THz-TDS spectrum by constructing a numerical model of the measured THz-TDS spectrum based upon an estimated complex index of refraction and then optimizing the estimated complex index of refraction by minimizing the error between the estimated and measured complex indices of refraction. In other words, the optimal estimated complex index of refraction is found to be the estimated complex index of refraction that produces a model THz-TDS spectrum that most closely matches the measured spectrum. Any known method may be used to determine the estimated complex index of refraction from the measured sample and one example of such a procedure is described in detail below. Once the estimated complex index of refraction is obtained, the complex permittivity may be determined using known relationships between the real and imaginary parts of the complex permittivity $\in'$ and $\in''$, respectively, and the index of refraction n and absorption coefficient α:

$$n = \sqrt{\frac{1}{2}\left[\sqrt{(\varepsilon')^2 + (\varepsilon'')^2} + \varepsilon'\right]} \quad (1)$$

$$\alpha = \frac{4\pi f}{c}\sqrt{\frac{1}{2}\left[\sqrt{(\varepsilon')^2 + (\varepsilon'')^2} - \varepsilon'\right]} \quad (2)$$

where the complex permittivity $\tilde{\in} = \in' + i\in''$.

Once the complex permittivity is determined, the volume fractions of the sample constituents may be determined using an effective medium theory and/or dielectric mixing law, as described in more detail below. More specifically, a dielectric mixing law may be used to combine a set of reference measurements thereby forming a model frequency dependent complex permittivity that is then compared to the complex permittivity determined from the THz spectrum measurements. For example, the reference measurements may be stored in memory, e.g., in a database such as dielectric constant database 111a and/or rock matrix database 111b or may be both stored in a single database. Examples of reference measurements are shown in FIGS. 4A, 4B, 5A and 5B. The final estimate for the volume fractions of the combination of reference materials is the combination of reference measurements that yields the lowest error match to the measured complex permittivity. The type of the constituents within the sample is an example of a physical property of the sample. Also, the final estimate of the constituent volume fractions is another example of a physical property of the sample. Furthermore, from the final estimates of the volume fractions, other physical properties of the sample may be determined, e.g., the porosity and water saturation may be determined. As used herein, porosity $\phi$ is defined as $\phi = V_V/V_T$ where $V_V$ is the void volume in the sample and $V_T$ is the total volume of the sample. Porosity is thus given by an estimate of the volume fraction of the rock matrix, $f_{matrix}$. Water saturation, $S_W$, is defined as $S_W = V_W/V_V$ where $V_W$ is the volume of water in the sample. Water saturation is thus given by $S_W = f_{water}/(1-f_{matrix})$ where $f_{water}$ is an estimate of the volume fraction of water in the sample.

In accordance with one or more embodiments, the complex index of refraction of the unknown sample may be determined from the THz-TDS spectrum as described below. With the THz-TDS spectrometer operating in transmission mode, as shown above in reference to FIG. 2, a THz pulse that has propagated through a sample may be written as $$e_{meas}(t) = e_0(t) * h(t) \quad (3)$$

where * denotes the convolution operator.

In other words, the measured pulse $e_{meas}(t)$, measured after passing through the sample, may be written as a convolution of the initial pulse $e_0(t)$ with a pulse response function of the sample given by h(t). Furthermore, the response function h(t) depends on the material parameters of the unknown sample. Then, according to the convolution theorem, Eq. (3) may be written in the frequency domain as $$E_{meas}(\omega) = E_0(\omega) \cdot H(\omega) \quad (4)$$

Thus, in a manner that corresponds to the response function h(t), the transfer function H(ω) depends on the material parameters of the sample. Accordingly, Eq. (3) may be rewritten in the form of an inverse Fourier transform $$e_{meas}(t) = \frac{1}{2\pi}\int_{-\infty}^{\infty} E_0(\omega) \cdot H(\omega) e^{i\omega t} d\omega \quad (5)$$

In accordance with one or more embodiments, a model pulse $e_m(t)$ may be constructed from Eq. (5) using a model transfer function $H_m(\omega)$ that itself depends on the model complex refractive index $\tilde{n}_m(\omega) = n_m(\omega) - i\kappa_m(\omega)$. The complex refractive index may then be found numerically by finding the model refractive index $\tilde{n}_m(\omega)$ that minimizes the error between $e_m(t)$ and $e_{meas}(t)$. In accordance with one or more embodiments, the error function used for the minimization may be of the form $$\text{ERROR} = \sum_t [e_{meas}(t) - e_m(t)]^2 \quad (6)$$

In accordance with one or more embodiments, the model pulse may be constructed in the Fourier domain with the help of Eq. (4):

$$E_m(\omega) = E_0(\omega) \cdot H_m(\omega) \quad (7)$$

and the model pulse may be reconstructed in the time domain using Eq. (3), or $$e_m(t) = \frac{1}{2\pi}\int_{-\infty}^{\infty} E_m(\omega) e^{i\omega t} d\omega \quad (8)$$

There are many different ways to construct $E_m(\omega)$ using model material parameters without departing from the scope for the present disclosure. For example, the discussion in Li et al., "Precisely [sic] optical material parameter determination by time domain waveform rebuilding with THz time-domain spectroscopy," Optics Communications 283, 4701 (2010), describes one such method, a portion of which is summarized here for convenience. As described in Li et al., multiple Fresnel reflections from the air-sample and/or sample-air interfaces may be taken into account for maximum accuracy depending on the temporal length of the THz acquisition. In accordance with one or more embodiments, the Fourier transform of the model pulse may be written as $$E_m(\omega) = E_0(\omega) P(\tilde{n}_0, L_0 - d) T_{01} P(\tilde{n}_1, d) T_{10} \sum_{i=0}^{n} (R_{10}^2 P(\tilde{n}_1, d)^2)^i \quad (9)$$

where $E_0(\omega)$ is the Fourier transform of the initial pulse; the propagation function $P(n, x) = e^{-j\omega \tilde{n} x/c_0}$ models the propagation of a pulse through a material having a complex refractive index $\tilde{n}$ and a length x; $\tilde{n}_0$ is the complex refractive index of air; $\tilde{n}_1$ is the complex refractive index of the sample;

d is the thickness of the sample; and $L_0$ is the distance between the front surface of the sample and the detector. Thus, the function $P(\tilde{n}_0, L_0-d)$ models the propagation of the pulse through the air separating the sample and the detector and the function $P(\tilde{n}_1, d)$ models the propagation of the pulse through the sample. Furthermore, the Fresnel reflection and transmission coefficients $T_{ij}$ and $R_{ij}$ model transmission and reflection, respectively, of a THz wave that is incident from material i and exits into material j. For example, the reflection coefficient at the interface of the sample and air is $R_{10}=(\tilde{n}_0-\tilde{n}_1)/(\tilde{n}_0+\tilde{n}_1)$ and the transmission coefficient at the same interface is $T_{10}=2\tilde{n}_1/(\tilde{n}_1+\tilde{n}_0)$. The summation term accounts for multiple "copies" of the initial pulse that result from multiple reflections inside the sample and is determined to be the largest integer that satisfies the inequality:

$$m \le \frac{1}{2}\left(\frac{c_0 t_{max}}{n_1 d} - 1\right),$$

where $t_{max}$ is the time window over which the THz-TDS spectrum is obtained. Furthermore, Eq. (9) may be written in terms of the measured reference pulse (i.e., the pulse that propagates through the system with no sample present) using the propagation function $P(n,x)$. Thus, the propagation of the reference pulse through the length $L_0$ in air may be modeled as $$E_{REF}(\omega) = E_0(\omega) P(\tilde{n}_0, L_0) \quad (10)$$

Thus, using Eq. (10), Eq. (9) may be rewritten as $$E_m(\omega) = E_{REF}(\omega) P(\tilde{n}_0, -d) T_{01} P(\tilde{n}_1, d) T_{10} \sum_{i=0}^{n} (R_{10}^2 P(\tilde{n}_1, d)^2)^i \quad (11)$$

For a given choice of the complex refractive index of the sample $\tilde{n}_1$, the modeled pulse $e_m(t)$ may be reconstructed from Eq. (11) using the inverse Fourier transform shown in Eq. (8). The initial guess for $\tilde{n}_1(\omega) = n_1(\omega) - i\kappa_1(\omega)$ may be found a number of ways. For example, they may be chosen using the so-called quasi analytic method (QA) (i.e., neglecting the aforementioned multiple internal reflections within the sample) where the measured transfer function is given simply by $$H_{meas}(\omega) = \frac{E_{meas}(\omega)}{E_{ref}(\omega)}.$$

Then the initial estimates may be written as follows $$n_1(\omega) = \arg[H_{meas}(\omega)] \frac{c_0}{\omega d} + n_0 \quad (12)$$

$$\kappa_1(\omega) = \ln\left[\frac{4 n_1(\omega)}{|H_{meas}(\omega)|(n_1(\omega)+1)^2}\right] \frac{c_0}{\omega d} \quad (13)$$

The final estimates for $n_1(\omega)$ and $\kappa_1(\omega)$ are then chosen as the $n_1(\omega)$ and $\kappa_1(\omega)$ that minimize the error between $e_{meas}$ and $e_m(t)$, e.g., according to Eq. (6). In accordance with one or more embodiments, any known numerical algorithm may be used for the error minimization, e.g., Nelder-Mead, or the like. Furthermore, in accordance with one or more embodiments, any form of error function may be used and, thus, the present disclosure is not limited to the form used in the example above.

Furthermore, while the above example used a THz-TDS spectrum as an example, any type of THz spectrum may be used without departing from the scope of the present disclosure. For example tunable continuous wave (CW) sources, e.g., those sources based on microwave systems, scaled up in frequency, may be used to obtain a THz spectrum. In accordance with one or more embodiments, a THz spectrum may be obtained using a CW source by measuring the THz power transmitted (or absorbed) through (by) the sample using a THz power detector. Furthermore phase information may be obtained from the power absorption spectrum using Kramers-Kronig relations. For example, one form of Kramers-Kronig relation relates the real part of the refractive index to the absorption coefficient $\alpha$:

$$n(\omega) = 1 + \frac{c}{\pi} \wp \int_0^{+\infty} \frac{\alpha(\Omega)}{\Omega^2 - \omega^2} d\Omega \quad (14)$$

where $\wp$ is the Cauchy principle value. Thus, using Eq. (14) the frequency dependent refractive index (real part) may be calculated from a measurement of the frequency dependent absorption losses of the sample. In another example, a quadrature detection scheme may be used to retrieve both the real (in phase) and imaginary (quadrature) components of the THz signal so that a measurement based on quadrature detection provides information that is substantially similar to that obtained using TDS.

FIGS. 4A, 4B, 5A, and 5B show frequency dependent index of refraction and frequency dependent absorption coefficient measurements made using reference samples of known composition, in accordance with one or more embodiments of the disclosure. Sample measurements, such as those shown in FIGS. 4A, 4B, 5A, and 5B, are similar to those that make up the dielectric constant database 111a and the rock matrix database 111b used in the system of FIG. 1. In accordance with one or more embodiments, the reference measurements may be stored as frequency dependent absorption coefficients and frequency dependent indices of refraction as is shown in FIGS. 4A, 4B, 5A, and 5B. Equivalently, the reference measurements may be reparameterized in terms of the real and imaginary part of the complex permittivity, e.g., by solving Eqs. (1) and (2) for $\in'$ and $\in''$.

In accordance with one or more embodiments, the reference samples may be pressed into pellets using high density polyethylene (an almost transparent material at terahertz frequencies) in order to assure homogeneous samples with well-known path lengths. Reference samples may include samples of known minerals and/or clays such as quartz, calcite, illite, cheto montmorillonite, Wyoming bentonite, smectite, or the like. In accordance with one or more embodiments, the thickness of the pellets may range from 1 mm to 4 mm depending on the absorption coefficient of the sample. In accordance with one or more embodiments, pressing parameters may be 5 to 15 tons of force using a 10 to 20 mm vacuum die held at pressure for 10 to 40 minutes. For example, the material added to the high density polyethylene may originate from core samples of rock formations containing unconventional oil or gas.

Further, in accordance with one or more embodiments, the unknown sample may be a core sample with a length of approximately 1 mm having polished ends to reduce scattering from rough surfaces. In other embodiments, core samples, or any other type of sample obtained in the field may be ground and pressed into pellets using high density polyethylene in order to assure homogenous samples with well-known path lengths. In accordance with one or more embodiments, the thickness of the pellet (along the direction of propagation of the THz radiation) ranges from 1 mm to 4 mm depending on the absorption coefficient of the sample. In accordance with one or more embodiments, pressing parameters may be 5 to 15 tons of force using a 10 to 20 vacuum die held at pressure for 10 to 40 minutes.

Figure 6:
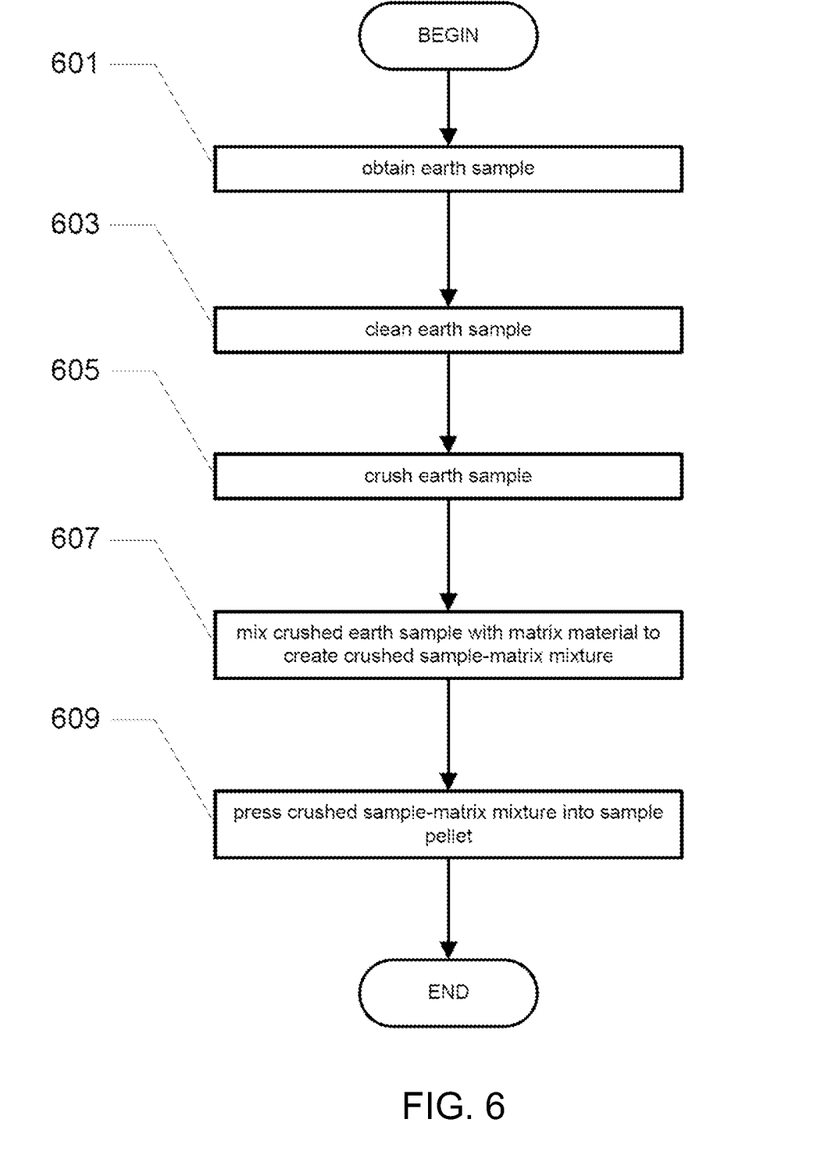
FIG. 6 shows a flow chart for a method of preparing a rock sample used for determining rock properties using terahertz-band dielectric measurements in accordance with one embodiment.

FIG. 6 shows an example method for preparation of a sample for analysis by, or use as a reference in, the system and method in accordance with one or more embodiments. While the various blocks in this flowchart are presented and described sequentially, one of ordinary skill will appreciate that, in accordance with one or more embodiments, at least a portion of the blocks may be executed in different orders, may be combined or omitted, and at least a portion of the blocks may be executed in parallel. In process 601, a raw earth sample is acquired, e.g., from drill cuttings, a core sample, or an outcrop sample. This sample may be an earth sample having an unknown, partially known, or completely known (e.g., if the sample is to be used as a reference sample) compositional makeup. In process 603, if desirable, the raw sample is cleaned, e.g., using solvent extraction or other methods, to remove drilling mud and/or formation fluids that may include, e.g., hydrocarbons or the like. In process 605, the cleaned sample is crushed using a sample grinder and/or mill. In accordance with one or more embodiments, the sample is crushed to obtain a crushed sample having particle sizes that are less than the wavelength of the terahertz radiation to be used for the analysis of the sample. For example, a electromagnetic wave of frequency 1 THz has a wavelength of about 300 microns. Thus, in accordance with one or more embodiments, the crushed sample particle size may be less than about 300 microns for 1 THz waves. In other embodiments, the crushed sample particle size may be substantially less than the wavelength of the THz wave, e.g., in a range of 1-100 microns. One of ordinary skill having the benefit of this disclosure will appreciate that the use of other THz wavelengths may lead to smaller or larger particle sizes for the crushed sample and thus the sizes disclosed herein are for example purposes. In process 607, the crushed sample is mixed with a matrix material that is substantially transparent to THz waves, and/or has a known complex permittivity in the THz range, e.g., powder high density polyethylene ("HDPE"), polytetrafluoroethylene (PTFE or TEFLON), polymethylpentene (TPX), or the like. In accordance with one or more embodiments, the crushed sample is mixed with the matrix material, e.g., HDPE, in a weight fraction ranging from 1:10 crushed sample to HDPE to 1:1 crushed sample to HDPE. In accordance with one or more embodiments, the combined weight of the HDPE and sample falls within a range of 300-700 mg. In process 609, the crushed sample HDPE mixture may be pressed into a sample pellet. For example, in accordance with one or more embodiments, samples in the range of 100 mg to 500 mg may be pressed by 5 to 15 tons of force using a 10 to 20 mm vacuum die held at pressure from 10 to 40 minutes.

The specific examples of the pellet fabrication method and the specific parameters for length, pressure, time, disclosed above are merely for the sake of example and are not meant to limit the scope of the present disclosure. Furthermore, one of ordinary skill will appreciate that the samples prepared by the above-described method may be used as reference samples (if made with samples having known constituents) or unknown samples used that may be later characterized using the method and system of determining rock properties using terahertz-band dielectric measurements in accordance with one or more embodiments.

Figure 7:
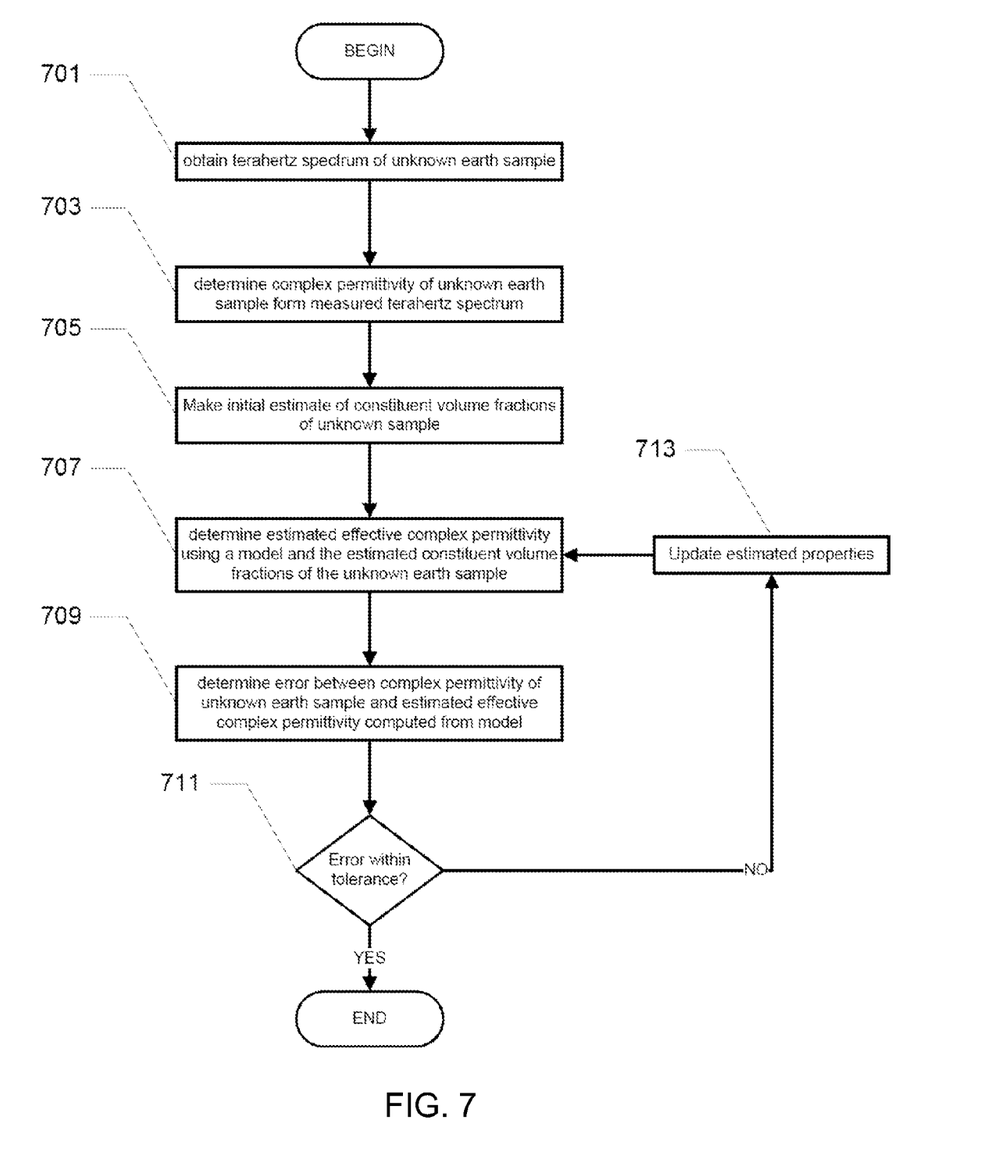
FIG. 7 shows a flow chart for a method of determining rock properties using terahertz-band dielectric measurements in accordance with one embodiment.

FIG. 7 shows a flow chart for a method of determining rock properties using terahertz-band dielectric measurements in accordance with one or more embodiments. While the various blocks in this flowchart are presented and described sequentially, one of ordinary skill will appreciate that, in accordance with one or more embodiments, at least a portion of the blocks may be executed in different orders, may be combined or omitted, and at least a portion of the blocks may be executed in parallel. Furthermore, the blocks may be performed actively or passively. For example, some blocks may be performed using polling or be interrupt driven in accordance with one or more embodiments. By way of an example, determination blocks may not use a processor to process an instruction unless an interrupt is received to signify that condition exists in accordance with one or more embodiments. As another example, determination blocks may be performed by checking a data value to test whether the value is consistent with a tested condition in accordance with one or more embodiments.

In process 701, a THz spectrum of an unknown rock sample is obtained, e.g., a THz-TDS spectrum as described above. In accordance with one or more embodiments, the rock sample may itself be a core sample obtained using a coring bit or downhole core sampling tool. In another example, the rock sample is a drill cutting from a wellbore, which is produced by a drilling process and brought to the surface by circulation of drilling mud. The THz spectrum may be obtained any number of ways without departing from the scope of the present disclosure. For example, the THz-spectrum may be retrieved from a database of previously measured THz spectra that are stored in a computer readable memory. In addition, the THz spectrum may be obtained directly from a terahertz time domain spectrometry system, or any other type of THz spectrometer, shortly after the measurement, and/or in real time as one or more THz measurements are made. In view of the above, the present disclosure is not limited to any particular method for obtaining a THz spectrum.

In process 703, the complex permittivity of the unknown sample is determined from the obtained THz spectrum. In accordance with one or more embodiments, the complex permittivity of the unknown sample may be obtained in a number of different ways. For example, the complex permittivity may be obtained using the THz spectrum and a reference spectrum taken using the THz spectrometry system without a sample in the system (i.e., a sample of ambient air). In accordance with one or more embodiments, the complex permittivity of the unknown sample is determined by first estimating the complex permittivity and then generating a model THz spectrum based on the estimated complex permittivity. Then the final estimate for the estimated complex permittivity is determined by choosing the permittivity that results in a model THz spectrum that most closely matches the measured THz spectrum. For example one such method is described above in reference to FIGS. 3A-3B. Determining the closest match may involve any type of numerical optimization or minimization routine, e.g., using a least squares technique that minimizes the difference squared between the measured THz spectrum and the model THz spectrum. In accordance with one or more embodiments, for the case of the THz spectrum that is a THZ-TDS spectrum, such an error may be quantified by the error function $$\text{ERROR} = \sum_t [e_{meas}(t) - e_m(t)]^2 \qquad (15)$$

where $e_{meas}(t)$ is the measured THz-TDS spectrum and $e_m(t)$ is the model THz-TDS spectrum. The error function embodied in Eq. (15) above is merely one example of many different forms of error functions that may be used to find the optimal model THz-TDS spectrum. Accordingly, any error function and any numerical method may be used without departing from the scope of the present disclosure. Furthermore, while the above example is set forth in the time domain, one of ordinary skill will also appreciate that the numerical computation may also be accomplished in the frequency domain without departing from the scope of the present disclosure. For example, for a CW based THz spectrometer the THz spectra may be measured directly, in which case the error function may take the form of $$\text{ERROR} = \sum_t [E_{meas}(\omega) - E_m(\omega)]^2$$

In accordance with one or more embodiments, it may actually be the complex refractive index $\tilde{n}_1(\omega) = n_1(\omega) - i\kappa_1(\omega)$ that is directly estimated when the model THz spectrum is determined, where the absorption coefficient $\alpha(\omega) = 2\omega\kappa(\omega)/c_0$. Accordingly, once $n_1(\omega)$ and $\kappa_1(\omega)$ are determined, these parameters may be converted into a complex permittivity $\tilde{\epsilon} = \epsilon' + i\epsilon''$ using Eqs. (1) and (2) above for the index of refraction and absorption coefficient. Eqs. (1) and (2) are reproduced below for convenience.

$$n = \sqrt{\frac{1}{2}\left[\sqrt{(\epsilon')^2 + (\epsilon'')^2} + \epsilon'\right]} \qquad (16)$$

$$\alpha = \frac{4\pi f}{c}\sqrt{\frac{1}{2}\left[\sqrt{(\epsilon')^2 + (\epsilon'')^2} - \epsilon'\right]} \qquad (17)$$

Accordingly, by measuring the THz spectrum of an unknown sample, the complex permittivity $\tilde{\epsilon}$ of the unknown sample is determined.

In process 705, an initial estimate of the volume fractions $f_i$ of the constituents of the unknown sample is made. For example, in the case of an unconventional core sample, prior measurements such as FTIR may be used to determine the rock matrix material. In accordance with one or more embodiments, the rock matrix material itself may be a mixture of various clays and/or minerals and, thus, the estimate of the volume fractions may include estimates of the volume fraction of various rocks and minerals, e.g., quartz, calcite, smectite, illite, cheto montmorillonite, and/or Wyoming bentonite. In addition, initial estimates may be made as to the volume fraction of various fluids contained within the rock matrix, e.g., volume fractions of water, ethanolamine, methyldiethanolamine, pyridine, ethanol, isopropanol, toluene, xylene, hexadecane, heptane, hexane, and/or various forms of crude oil may also be estimated in process 705.

In process 707, a model complex permittivity is determined using the estimated volume fractions and a dielectric mixing law obtained from an effective medium theory, such as the Maxwell-Garnett equation:

$$\frac{\epsilon_E - \epsilon_n}{\epsilon_E + 2\epsilon_n} = \sum_{i=1}^{n-1} f_i \frac{\epsilon_i - \epsilon_n}{\epsilon_i + 2\epsilon_n} \qquad (18)$$

where $\epsilon_i$, $\epsilon_n$, and $\epsilon_E$ are the dielectric constants of the inclusion constituents, the host constituent, and the effective medium, respectively, and $f_i$ is the volume fraction of the given inclusion constituent defined such that $\Sigma_{i=1}^{n}f_i = 1$. Without departing from the scope of the present disclosure, any type of model may be used to form the effective medium, e.g., Maxwell Garnett (MG) model, Polder and van Santen (PvS) model, Bruggeman model, and a Landau, Lifshitz, and/or Looyenga (LLG) models may be used. Further details regarding effective medium theories and dielectric mixing laws generally are available in T. Ervasti et al. APPLIED SPECTROSCOPY, 66, 319-323 (2012), and, e.g., in *Recent Optical and Photonic Technologies*, Ki Young Kim, ed. (2010).

In process 709, the error between the frequency dependent model complex permittivity $\epsilon_E(\omega)$ and the frequency dependent measured complex permittivity $\tilde{\epsilon}(\omega)$ is determined. In accordance with one or more embodiments, such an error may be quantified by an error function $$\text{ERROR} = \sum_t [\tilde{\epsilon}(\omega) - \epsilon_E(\omega)]^2 \qquad (19)$$

However, the error function embodied in Eq. (17) above is merely one example of many different forms of error functions that may be used to find the constituent volume fractions.

In process 711, the determined error between the model complex permittivity $\epsilon_E(\omega)$ and the measured complex permittivity $\tilde{\epsilon}(\omega)$ is compared against a predetermined threshold. If the error is greater than the threshold value, the estimated sample properties used to generate the model, e.g., the estimated volume fractions and/or the number and type of constituents, are updated. In accordance with one or more embodiments, any type of numerical routine may be used to update model and compute the error, e.g., by way of a nonlinear least squares fitting routine, or the like.

If it is determined in process 711 that the error is below the predetermined threshold then the set, or subset, of most recent model parameters may output as the final estimate for the unknown sample. In one example, the output may be stored in memory or sent to a display device for presentation to user. Accordingly, the constituents that make up the unknown sample and/or the volume fractions of these constituents are determined.

Figure 8A:
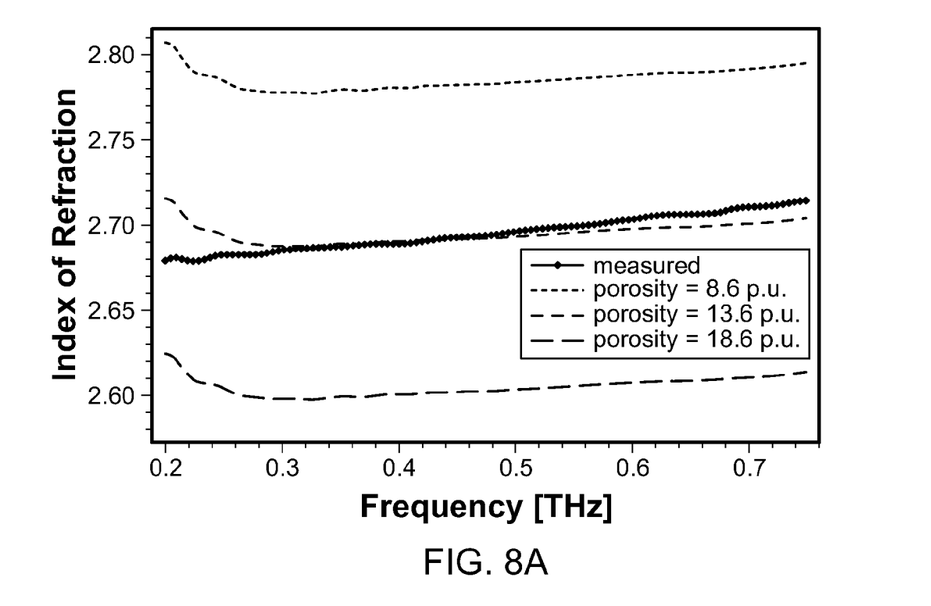
FIGS. 8A-8B show examples of a numerical model plotted for different values of the model parameters that are adjusted during the numerical fitting routine.
Figure 8B:
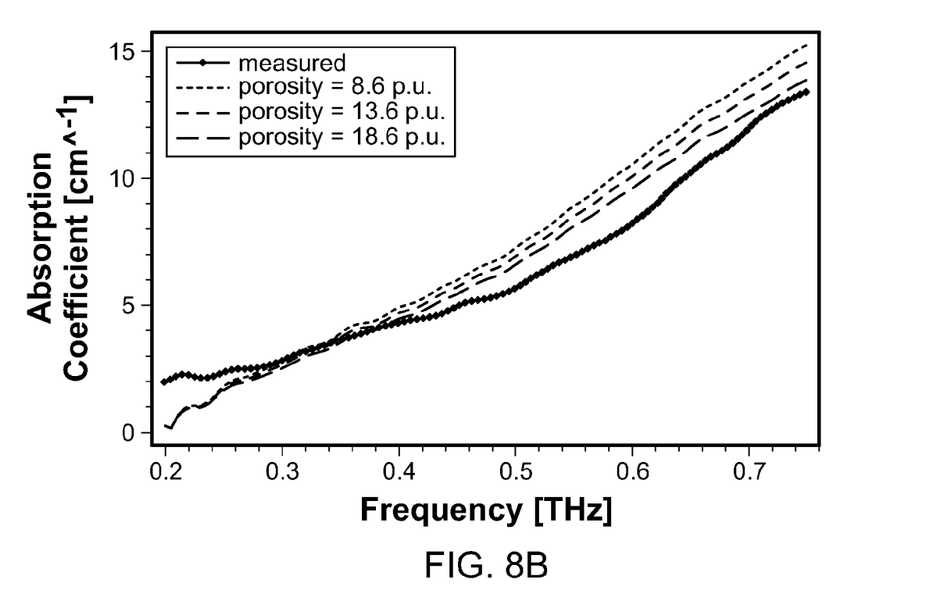

FIGS. 8A-8B show examples of a numerical model plotted for different values of the model parameters that are adjusted during the numerical fitting routine. The dotted lines show the measured values while the solid lines show the calculated parameters given the porosity. As described above, the porosity $\phi$ is defined as $\phi = V_P/V_T$ where $V_P$ is the void volume in the sample and $V_T$ is the total volume of the sample. Porosity is thus given by an estimate of the volume fraction of the rock matrix, $f_{matrix}$. The fit to the measured data that produces the minimum error occurs at a porosity of 13.6 p.u. Note this sample has been cleaned so that there are no hydrocarbons or water present in it. As such, the water and oil saturations are forced to 0 in the fit.

Embodiments may be implemented on virtually any type of computing system regardless of the platform being used.

Figure 9:
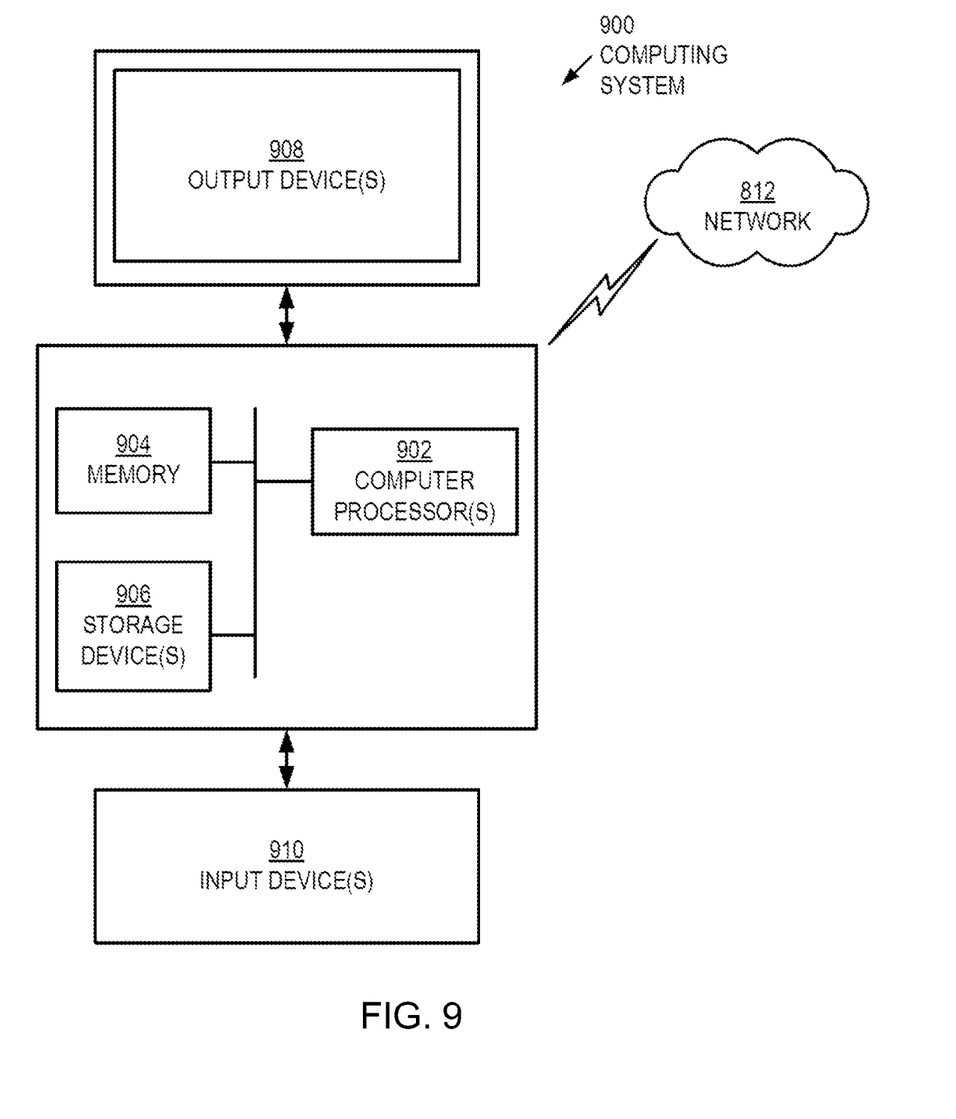
FIG. 9 shows an example of a computer system that may be used to implement the system and method in accordance with one embodiment.

For example, the computing system may be one or more mobile devices (e.g., laptop computer, smart phone, personal digital assistant, tablet computer, or other mobile device), desktop computers, servers, blades in a server chassis, or any other type of computing device or devices that includes at least the minimum processing power, memory, and input and output device(s) to perform one or more embodiments. For example, as shown in FIG. 9, the computing system 900 may include one or more computer processor(s) 902, associated memory 904 (e.g., random access memory (RAM), cache memory, flash memory, etc.), one or more storage device(s) 906 (e.g., a hard disk, an optical drive such as a compact disk (CD) drive or digital versatile disk (DVD) drive, a flash memory stick, etc.), and numerous other elements and functionalities. The computer processor(s) 902 may be an integrated circuit for processing instructions. For example, the computer processor(s) may be one or more cores, or micro-cores of a processor. The computing system 900 may also include one or more input device(s) 910, such as a touchscreen, keyboard, mouse, microphone, touchpad, electronic pen, or any other type of input device. Further, the computing system 900 may include one or more output device(s) 908, such as a screen (e.g., a liquid crystal display (LCD), a plasma display, touchscreen, cathode ray tube (CRT) monitor, projector, or other display device), a printer, external storage, or any other output device. One or more of the output device(s) may be the same or different from the input device(s). The computing system 900 may be connected to a network 912 (e.g., a local area network (LAN), a wide area network (WAN) such as the Internet, mobile network, or any other type of network) via a network interface connection (not shown). The input and output device(s) may be locally or remotely (e.g., via the network 912) connected to the computer processor(s) 902, memory 904, and storage device(s) 906. Many different types of computing systems exist, and the aforementioned input and output device(s) may take other forms.

Software instructions in the form of computer readable program code to perform embodiments may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s), is configured to perform embodiments.

Further, one or more elements of the aforementioned computing system 900 may be located at a remote location and connected to the other elements over a network 912. Further, embodiments may be implemented on a distributed system having a plurality of nodes, where each portion may be located on a different node within the distributed system. In one embodiment, the node corresponds to a distinct computing device. Further, the node may correspond to a computer processor with associated physical memory. The node may correspond to a computer processor or micro-core of a computer processor with shared memory and/or resources.

The systems and methods disclosed herein generally relate to a method for the characterization of the dielectric response of unknown samples, e.g., unknown unconventional core samples. It will be appreciated that the same systems and methods may be used for performing subsurface analysis in fields such as oilfield, mining, water retrieval, or in any field where sample characterization is desired. Furthermore, in accordance with one or more embodiments, the system may be deployed as a stand-alone analytical instrument, e.g., as a lab-based analytical instrument or as ruggedized unit for field work, or as part of a downhole logging tool for in situ formation characterization, e.g., as part of a wireline tool, a logging while drilling ("LWD") tool, or a measurement while drilling ("MWD") tool. For example, in an oilfield application, the system and methods disclosed herein may take the form of, or be implemented within, a downhole tool for determining the composition of a core sample. In other embodiments, the system and methods may be deployed uphole as an analytical instrument for analysis on any type of unknown sample. The systems and methods disclosed herein are not limited to the above-mentioned applications and these applications are included herein merely as a subset of examples. Furthermore, portions of the systems and methods may be implemented as software, hardware, firmware, or combinations thereof.

Although the preceding description has been described herein with reference to particular means, materials and embodiments, it is not intended to be limited to the particulars disclosed herein; rather, it extends to functionally equivalent structures, methods and uses, such as are within the scope of the appended claims.

What is claimed is:

1. A method of analyzing a physical property of a sample, the method comprising:
    operating a terahertz spectrometer to obtain an electromagnetic spectrum of the sample, wherein the electromagnetic spectrum comprises a terahertz spectrum;
    computing a sample complex permittivity from the electromagnetic spectrum of the sample;
    estimating types of constituents and constituent fractions;
    computing an estimated effective complex permittivity based upon a model and the constituent fractions; and
    comparing the computed sample complex permittivity with the estimated effective complex permittivity to determine the physical property of the sample.

2. The method of claim 1, wherein the model is determined using a dielectric mixing law that combines known reference complex permitivities for each of the constituents using the constituent fractions.

3. The method of claim 2, wherein the comparing further comprises:
    minimizing a difference between the estimated effective complex permittivity and the sample complex permittivity by varying the estimated constituent fractions; and
    determining the physical property of the sample using the estimated constituent fractions that minimize the difference between the estimated effective complex permittivity and the sample complex permittivity.

4. The method of claim 3, wherein minimizing the difference comprises using a nonlinear least squares fit of the sample complex permittivity to the estimated effective complex permittivity using at least one estimated constituent fraction as a fitting parameter.

5. The method of claim 2, wherein one of the estimated constituent fractions is a volume fraction of a rock matrix of the sample.

6. The method of claim 5, wherein one of the estimated constituent fractions is selected from a group consisting of water volume fraction, oil volume fraction, and gas volume fraction.

7. The method of claim 2, wherein one of the estimated fractions is a volume fraction of a mineral constituent of the sample.

8. The method of claim 7, wherein the mineral constituent of the sample is selected from a group consisting of smectite and illite.

9. The method of claim 2, wherein one of the estimated constituent fractions is a volume fraction of smectite and another of the estimated fractions is a volume fraction of illite.

10. The method of claim 2, wherein an initial estimate of at least one of the estimated fractions is obtained by Fourier transform spectroscopy of the sample.

11. The method of claim 2, wherein the dielectric mixing law is selected from a group consisting of a Maxwell Garnett (MG) model, Polder and van Santen (PvS) model, Bruggeman model, and a Landau, Lifshitz, Looyenga (LLG) model.

12. The method of claim 1, further comprising:
creating the sample, wherein the creating comprises:
obtaining a raw earth sample;
crushing the raw earth sample to create a crushed earth sample;
mixing the crushed earth sample with a matrix material to create a crushed sample-matrix mixture; and
pressing the crushed sample-matrix mixture to form the sample.

13. The method of claim 1, comprising obtaining the electromagnetic spectrum by terahertz time domain spectrometry.

14. A system for terahertz ("THz") band dielectric measurements, the system comprising:
a THz spectrometer configured to obtain a THz spectrum of a sample; and
an analysis module configured to:
receive the THz spectrum of the sample;
compute a sample complex permittivity from the THz spectrum of the sample;
estimate types of constituents and constituent fractions;
compute an estimated effective complex permittivity based upon a model and the constituent fractions; and
compare the computed sample complex permittivity with the estimated effective complex permittivity to determine a physical property of the sample.

15. The system of claim 14, wherein the analysis module further comprises:
a sample modeling engine configured determine the model of the sample using a dielectric mixing law that combines a plurality of known reference complex permitivities for each of the constituents using the estimated constituent fractions.

16. The system of claim 15, wherein the analysis module further comprises:
an error estimation engine configured to:
minimize a difference between the estimated effective complex permittivity and the sample complex permittivity by varying the estimated constituent fractions; and
determine the physical properties of the sample using the estimated constituent fractions that minimize the difference between the estimated effective complex permittivity and the sample complex permittivity.

17. The system of claim 15, wherein one of the estimated constituent fractions is a volume fraction of a rock matrix of the sample.

18. The system of claim 17, wherein one of the estimated constituent fractions is selected from a group consisting of water volume fraction, oil volume fraction, and gas volume fraction.

19. The system of claim 14, wherein one of the estimated constituent fractions is a volume fraction of smectite and another of the estimated fractions is a volume fraction of illite.

20. The system of claim 14, wherein one of the estimated constituent fractions is a volume fraction of a mineral constituent of the sample.

21. The system of claim 20, wherein the mineral constituent of the sample is selected from a group consisting of smectite and illite.

22. The system of claim 14, wherein the THz spectrometer is configured as a THz time domain spectrometer.

23. A non-transitory computer readable medium comprising computer readable program code embodied therein, that, when executed on a processor, causes the processor to:
receive an electromagnetic spectrum of a sample that comprises a terahertz spectrum;
compute a sample complex permittivity from the electromagnetic spectrum of the sample;
estimate types of constituents and constituent fractions;
compute an estimated effective complex permittivity based upon a model and the constituent fractions; and
compare the computed sample complex permittivity with the estimated effective complex permittivity to determine a physical property the sample.

24. The non-transitory computer readable medium of claim 23, wherein the model is determined using a dielectric mixing law that combines a plurality of known reference complex permitivities for each of the constituents using the constituent fractions.

25. The non-transitory computer readable medium of claim 24, further comprising computer readable program code embodied therein, that, when executed on a processor, causes the processor to:
compare the computed sample complex permittivity with the estimated effective complex permittivity by minimizing a difference between the estimated effective complex permittivity and the sample complex permittivity by varying the estimated constituent fractions; and
determine the physical property of the sample using the estimated constituent fractions that minimize the difference between the estimated effective complex permittivity and the sample complex permittivity.

26. The non-transitory computer readable medium of claim 24, wherein one of the estimated fractions is a volume fraction of a rock matrix of the sample.

27. The non-transitory computer readable medium of claim 24, further comprising computer readable program code embodied therein, that, when executed on a processor, causes the processor to obtain the electromagnetic spectrum of the sample using terahertz time domain spectroscopy.

28. The non-transitory computer readable medium of claim 24, wherein one of the estimated constituent fractions is a volume fraction of smectite and another of the plurality of estimated fractions is a volume fraction of illite.

29. The non-transitory computer readable medium of claim 24, wherein one of the estimated constituent fractions is a volume fraction of a mineral constituent of the sample.

30. The non-transitory computer readable medium of claim 29, wherein the mineral constituent of the sample is selected from a group consisting of smectite and illite.

* * * * *